United States Patent
Deklotz et al.

(10) Patent No.: US 11,554,126 B2
(45) Date of Patent: Jan. 17, 2023

(54) METHODS OF TREATING RESIDUAL LESIONS OF VASCULAR ANOMALIES

(71) Applicants: Georgetown University, Washington, DC (US); MedStar Health, Columbia, MD (US)

(72) Inventors: Cynthia Marie Carver Deklotz, Bethesda, MD (US); Michael Andrew Cardis, Pittsburgh, PA (US)

(73) Assignees: Georgetown University, Washington, DC (US); MedStar Health, Columbia, MD (US)

( * ) Notice: Subject to any disclaimer, the term of this patent is extended or adjusted under 35 U.S.C. 154(b) by 0 days.

(21) Appl. No.: 16/772,630

(22) PCT Filed: Dec. 17, 2018

(86) PCT No.: PCT/US2018/066054
§ 371 (c)(1),
(2) Date: Jun. 12, 2020

(87) PCT Pub. No.: WO2019/118979
PCT Pub. Date: Jun. 20, 2019

(65) Prior Publication Data
US 2020/0384000 A1  Dec. 10, 2020

Related U.S. Application Data

(60) Provisional application No. 62/599,531, filed on Dec. 15, 2017.

(51) Int. Cl.
*A61K 31/575* (2006.01)
*A61K 47/54* (2017.01)
*A61P 9/14* (2006.01)
*A61K 9/00* (2006.01)
*A61K 47/02* (2006.01)
*A61K 47/10* (2017.01)

(52) U.S. Cl.
CPC .......... *A61K 31/575* (2013.01); *A61K 9/0019* (2013.01); *A61K 47/02* (2013.01); *A61K 47/10* (2013.01); *A61K 47/54* (2017.08); *A61K 47/542* (2017.08); *A61P 9/14* (2018.01)

(58) Field of Classification Search
CPC ..................................................... A61K 31/575
USPC .......................................................... 514/575
See application file for complete search history.

(56) References Cited

U.S. PATENT DOCUMENTS

| 5,122,520 A * | 6/1992 | Azria | .......... C07J 41/0061 514/182 |
| 2005/0158408 A1* | 7/2005 | Yoo | ................ A61K 47/36 514/561 |

FOREIGN PATENT DOCUMENTS

| WO | 2013038195 A2 | 3/2013 |
| WO | 2013038195 A3 | 7/2013 |
| WO | 2016172635 A1 | 10/2016 |
| WO | WO 2016/172635 | * 10/2016 |

OTHER PUBLICATIONS

Moroi, Journal of Lipid Research vol. 33, 1992.*
Dayan, Dermatologic Surgery: Nov. 2016—vol. 42, p. S263-S270.*
Sepulveda, Semin Plast Surg 2014;28:49-57.*
Cardis et al., Intralesional Deoxycholic Acid Treatment for Fibrofatty Residua of InvolutedInfantile Hemangiomas: A Novel Therapeutic Approach, JAMA Dermatol., Jun. 2018 [Retrieved on Feb. 8, 2019], Retrieved from the internet: Abstract.
Center for Drug Evaluation and Research, App. No. 2063330rig1s000, ClinicalPharmacology and Biopharmaceutics Review(s), May 13, 2014 [Retrieved on Feb. 7, 2019].Retrieved from the Internet: Cover Page, pp. 1-38, Filing Memorandum pp. 8-12.
International Search Report and Written Opinion issued in PCT/US2018/066054 dated Mar. 5, 2019.
Sepulveda et al., Vascular Tumors, Seminars in Plastic Surgery, vol. 28, No. 2, 2014 [Retrieved on Feb. 7, 2019]. Retrieved from the Internet: pp. 49-57.
Extended European Search Report issued in EP App No. 18889060.2 dated Aug. 10, 2021.
Ma J et al., "Ursodeoxycholic acid inhibits endothelin-1 production in human vascular endothelial cells", European Journal of Pharmacology, Elsevier Science, vol. 505, No. 1-3, Nov. 28, 2004, pp. 67-74.

* cited by examiner

*Primary Examiner* — Nizal S Chandrakumar
(74) *Attorney, Agent, or Firm* — Potomac Law Group, PLLC

(57) ABSTRACT

Compositions comprising bile acids or their salts and methods of use thereof for the treatment of residual lesions of vascular anomalies.

16 Claims, 2 Drawing Sheets

FIG. 1A-B

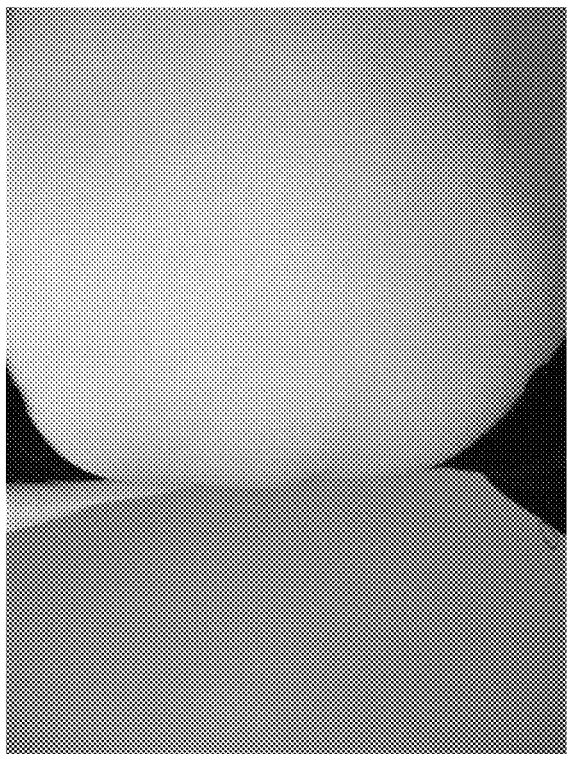
FIG. 2A-B

METHODS OF TREATING RESIDUAL LESIONS OF VASCULAR ANOMALIES

CROSS-REFERENCE TO RELATED APPLICATIONS

This is a national stage application of PCT/US2018/066054 filed Dec. 17, 2018 and claims priority to U.S. Provisional Patent Application Ser. No. 62/599,531 filed on Dec. 15, 2017, each of which is incorporated herein by reference in its entirety.

TECHNICAL FIELD OF THE INVENTION

The present disclosure relates to the technical fields of tumor biology and medicine.

BACKGROUND OF THE INVENTION

Vascular anomalies encompass a variety of rare and often complex tumors, malformations, vascular birthmark-producing syndromes that are produced by some localized defect in one or more elements of the vasculature (i.e., arteries, veins, capillaries and lymphatics). As their name suggests, vascular anomalies are primarily of a vascular nature and tend to actively profilerate. However, in many cases these anomalies comprise residual lesions that form once the anomaly has entered a non-proliferating stage. These residual lesions have a vascular component, but also have a fibrous or fibro-fatty tissue component as well.

Infantile hemangiomas (IH) are the most common soft tissue tumor of infancy with a prevalence of approximately 4.5%. They appear shortly after birth, grow to peak size by about nine months of age, and then involute over months to years. When left untreated, up to 70% of the time, the process of vascular degeneration results in permanent sequelae such as, telangiectasia, anetoderma, and/or excess fibrofatty tissue, all of which can cause significant cosmetic or functional concerns.

IHs have a distinct natural history involving three stages. An early proliferative phase is characterized by rapid growth of abnormal blood vessels during the first 6 months of life and extends to the first 10-12 months of life. This proliferative stage is followed by a plateau stage and then an involuting stage starting at about 1 year of age that may continue for several years. Finally, the IH becomes involuted, which can comprise one or more subtypes: atrophic scars, fibrofatty remnants (FFR), residual telangiectasia, and residual lesions or discoloration. Anetoderma, or macular atrophy, is another condition associated with involuted IH.

Congenital hemangioma is a vascular lesion that is present and fully grown at birth.

Kaposiform hemangiomendothelioma (KHE) is a rare vascular tumor. It is usually seen at birth or as a newborn. KHE is most common on the trunk, arms, legs and back, but is sometimes seen on the head or neck.

A tufted angioma is a similar to KHE, and there is some thought that it may be a mild form of KHE.

Lymphatic malformations comprise a collection of lymphatic channels in loose connective tissue stroma, and result in fluid collecting in tissues.

Commonly used options for treating vascular anomalies include embolization, radiation, laser therapy, sclerotheapy, and surgery. However, these existing treatment options are associated with inherent risks related to surgery and anesthesia, such as scarring, nerve damage, infection, bleeding, and tissue necrosis. Additionally, the cost associated with these treatment options is an additional barrier for many patients. Thus, there is a need in the art for non-surgical, cost-effective therapeutic approaches to treating residual lesions of vascular anomalies, which improve cosmetic and functional outcomes and lower the risks of adverse side-effects associated with presently available treatment options.

BRIEF SUMMARY OF THE INVENTION

The present disclosure relates to the treatment of a patient having a residual lesion of a vascular anomaly. In a particular embodiment, the vascular anomaly is an infantile hemangioma. In an another embodiment, the vascular anomaly is an involuted infantile hemangioma. In particular embodiments, the involuted infantile hemangioma comprises a sequelae. In certain embodiments, the sequelae is or comprises telangiectasia. In certain embodiments, the sequelae is or comprises fibrofatty tissue or residue (FFR). In certain embodiments, the sequelae is or comprises anetoderma. In some embodiments, the anetoderma may be associated with or the result of a disorder or condition that is not a vascular anomaly. In an another embodiment, the vascular anomaly is a congenital hemangioma. In an another embodiment, the vascular anomaly is a kaposiform hemangiomendothelioma. In an another embodiment, the vascular anomaly is a tufted angioma. In an another embodiment, the vascular anomaly is a lymphatic malformation.

In some aspects of the disclosure, treatment comprising contacting the residual lesion with a composition comprising a pharmaceutically-acceptable formulation comprising at least one bile acid or its salt. In a particular embodiment, the bile acid is cholic acid. In an another embodiment, the bile acid is glycocholic acid. In an another embodiment, the bile acid is taurocholic acid. In an another embodiment, the bile acid is deoxycholic acid. In an another embodiment, the bile acid is chenodeoxycholic acid. In an another embodiment, the bile acid is glycochenodeoxycholic acid. In an another embodiment, the bile acid is tautochenodeoxycholic acid. In an another embodiment, the bile acid is lithochlic acid. In an another embodiment, the bile acid is 7-alpha-dehydroxylate. In an another embodiment, the bile acid is ursodeoxycholic acid. In an another embodiment, the bile acid is obeticholic acid. In an another embodiment, the bile acid is a dihydroxy- or trihydroxy-bile acid. In some embodiments, the bile acid is conjugated to taurine or glycine.

In some aspects of the disclosure, the composition is administered to the patient as an aqueous solution. In some embodiments, the solution comprises deoxycholic acid at a concentration of about 1% w/v to about 5% w/v. In some embodiments, the solution comprises sodium deoxycholate. In a particular embodiment, the aqueous pharmaceutical formulation comprises deoxycholic acid at a concentration of 10 mg/mL; benzyl alcohol at a concentration of 9 mg/mL; dibasic sodium phosphate at a concentration of 1.42 mg/mL; sodium chloride at a concentration of 4.38 mg/mL; sodium hydroxide at a concentration of 1.43 mg/mL; and a pH of about 8.3.

In some aspects of the disclosure, the composition is administered to the patient only one time. In some aspects of the disclosure, the composition is administered to the patient more than once. In some aspects of the disclosure, the composition is administered intralesionally. In some aspects of the disclosure, the duration of treatment comprising multiple administrations takes place over the course of a month, two months, three months or even a year or more. In some aspects of the disclosure, the duration of treatment is determined by a particular endpoint, e.g., a duration effective to achieve at least a 5%, 10%, 25%, or 50% reduction in the size of the lesion. An improvement in one or more additional symptoms of the residual lesion (e.g., pain, discoloration) may also be used to determine the duration of treatment.

The present disclosure also relates to the use of a pharmaceutically-acceptable formulation comprising at least one bile acid or its salt for the treatment of a residual lesion of a vascular anomaly in a patient in need thereof. The present disclosure also relates to the use of a pharmaceutically-acceptable formulation comprising at least one bile acid or its salt in the manufacture of a medicament for the treatment or the treatment of a residual lesion of a vascular anomaly in a patient in need thereof. The present disclosure also relates a composition such as those described herein above for use in the treatment treatment of a residual lesion of a vascular anomaly in a patient in need thereof.

BRIEF DESCRIPTION OF THE SEVERAL VIEWS OF THE DRAWINGS

FIGS. 1A-1B. Pre-treatment: Frontal and oblique baseline views of a fibrofatty residua (FFR) from an involuted infantile hemangioma on the right flank measuring 0.8 cm high and 7.5 cm wide.

FIGS. 2A-2B. Post-treatment: Frontal and oblique views of the FFR showing significant improvement after two series of intralesional deoxycholic acid (DCA). Final measurement is 0.2 cm high and 6.4 cm wide.

DETAILED DESCRIPTION OF THE INVENTION

As provided herein, the present disclosure related to addressing the aforementioned challenges and unmet needs by providing, inter alia, therapeutic compositions comprising bile acids (e.g., deoxycholic acid (DCA)) and/or their salts in pharmaceutically-acceptable formulations and methods of use thereof for the non-surgical treatment of residual lesions of vascular anomolies. Administration routes, treatment regimens using the therapeutic compositions, and article of manufactures, such as a kit or a system comprising any of the therapeutic compositions, are also disclosed.

Unless defined otherwise, all technical and scientific terms used herein have the same meaning as commonly understood by one of ordinary skill in the art in the fields of tumor biology and dermatology. For example, *Stedman's Medical Dictionary*, 28th ed.; *Robbins Basic Pathology*, 9th ed., New York, N.Y., Elsevier, 2012; *Remington's Pharmaceutical Sciences*, provide one of skill in the art with a general dictionary of many of the terms used herein. Additional definitions are set forth throughout the detailed description.

Therapeutic Compositions and Pharmaceutical Formulations

The present disclosure relates to therapeutic compositions that comprise at least one pharmacologically-active bile acid or salt, optionally at least one pharmaceutically-acceptable excipient, and optionally one or more additional active ingredients, analgesics or dispersion agents and their use in treating residual lesions of vascular anomalies.

As used herein, "pharmaceutically acceptable" refers to an ingredient or material that is not biologically or otherwise undesirable, i.e., the ingredient or material may be incorporated into a pharmaceutical composition administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug Administration. "Pharmacologically active" (or simply "active") as in a "pharmacologically active" derivative or analog, refers to a derivative or analog having the same type of pharmacological activity as the parent compound and approximately equivalent in degree.

As used herein, the term "bile acid" refers to steroid acids found predominantly in the bile of mammals and other vertebrates. Primary bile acids are those synthesized by the liver. Secondary bile acids result from bacterial actions in the colon. They play an important role in the digestion and absorption of fat. Exemplary bile acids that are contemplated by the present disclosure include, but are not limited to, cholic acid, glycocholic acid, taurocholic acid, deoxycholic acid, chenodeoxycholic acid, glycochenodeoxycholic acid, tautochenodeoxycholic acid, lithochlic acid, 7-alpha-dehydroxylate, ursodeoxycholic, obeticholic acid, dihydroxy- and trihydroxy-bile acids.

The structures of particular bile acids are shown below:

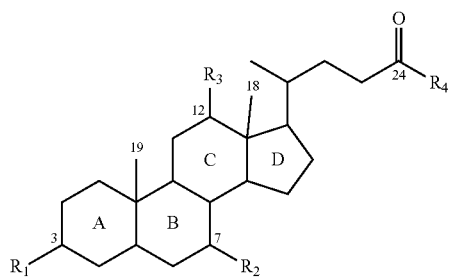

| Name | $R_1$ | $R_2$ | $R_3$ | $R_4$ |
|---|---|---|---|---|
| Cholic acid | OH | OH | OH | OH |
| Chenodeoxycholic acid | OH(α) | OH(α) | H | OH |
| Deoxycholic acid | OH | H | OH | OH |
| Ursodeoxycholic acid | OH(α) | OH(β) | H | OH |
| Lithocholic acid | OH | H | H | OH |
| Glycocholic acid | OH | OH | OH | $NHCH_2COO^+$ |
| Taurocholic acid | OH | OH | OH | $NHCH_2CH_2SO_2^+$ |

As used herein, the term "bile salt" refers to a salt (e.g., sodium or potassium) of the conjugate of any bile acid with either glycine or taurine. Certain embodiments relate to stereoisomers of any of the bile acids described herein, including intermediates in the synthesis of those bile acids and to pharmaceutically acceptable salts thereof. In other embodiments, the bile salt is a synthetic bile salt. See, e.g., U.S. Pat. No. 8,461,140, the disclosure of which is incorporated by reference herein.

Bile salts constitute a large family of molecules, composed of a steroid structure with four rings (A-D), a five- or eight-carbon side-chain terminating in a carboxylic acid, and several hydroxyl groups, the number and orientation of which differs among the specific bile salts.

The general chemical structure of bile salts is shown below:

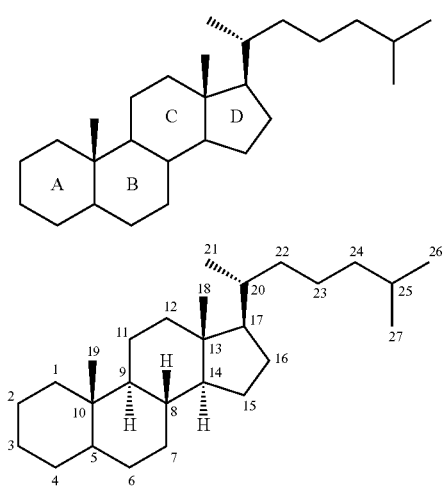

Suitable concentrations of bile acids or bile salts contemplated for use in the therapeutic compositions described and provided herein include, without limitation, a concentration range of about 0.001% up to about 50% w/v and any fraction of a percentage within these two values. In certain embodiments, the therapeutic compositions comprise bile salts in an amount (w/v) of about 0.1%, about 0.5%, about 1%, about 1.5%, about 2%, about 2.5%, about 3%, about 3.5%, about 4%, about 4.5%, about 5%, about 10%, up to about 50%. It is understood that the final concentration is dependent on many factors known to persons skilled in the art including, but not limited to, location and size of the treatment site (as discussed below).

In certain embodiments, the present disclosure provides a pharmaceutical formulation comprising DCA (3α,12α-dihydroxy-5β-cholan-24-oic acid) or a pharmaceutically acceptable salt thereof. An exemplary formulation comprising 10 mg/mL DCA is shown in Table 1.

TABLE 1

| | |
|---|---|
| DCA | 10 mg |
| Benzyl alcohol | 9 mg |
| Dibasic sodium phosphate | 1.42 mg |
| Sodium chloride | 4.38 mg |
| Sodium hydroxide | 1.43 mg |
| Water, USP | 1 mL |

An acid (e.g., hydrochloric acid) and/or base (e.g., sodium hydroxide) is added as necessary to adjust the formulation to a desired pH (e.g., 8.3).

As used herein, a "residual lesion" refers to a lesion that is produced by a vascular anomaly but is not tumorous in nature, i.e., the vascular anomaly is in a non-proliferative stage or state. A "residual lesion" also comprises at least some fibrous or fibrofatty tissue or cells and is not purely vascular in nature.

Therapeutic compositions described herein can include other active ingredients such as, without limitation, and in any compatible combination, anti-inflammatory agents and analgesics. Therapeutic compositions described herein can also include pharmaceutically acceptable excipients, dispersion agents, and penetration enhancers.

Anti-inflammatory agents suitable for use with the therapeutic compositions described herein can be either steroidal anti-inflammatory agents or non-steroidal anti-inflammatory agents. Suitable steroidal anti-inflammatory agents include, although are not limited to, corticosteroids such as hydrocortisone, hydroxyl triamcinolone alphamethyl dexamethasone, dexamethasone-phosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclarolone acetonide, fludrocortisone, flumethasone pivalate, fluosinolone acetonide, fluocinonide, flucortine butylester, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenalone acetonide, medrysone, amciafel, amcinafide, betamethasone and the balance of its esters, chloroprednisone, chlorprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylproprionate, hydrocortamate, meprednisone, paramethasone, prednisolone, prednisone, beclomethasone dipropionate, betamethasone dipropionate, triamcinolone, or mixtures thereof as appropriate.

Suitable non-steroidal anti-inflammatory agents include, but are not limited to: the oxicams, such as piroxicam, isoxicam, tonexicam, sudoxicam, and CP-14,304; the salicylates, such as salicylic acid, aspirin, disalcid, benorylate, trilisate, safapryn, solprin, diflunisal, and fendosal; the acetic acid derivatives, such as diclofenac, fenclofenac, indomethacin, sulindac, tolmetin, isoxepac, furofenac, tiopinac, zidometacin, acematacin, fentiazac, zomepiract, clidanac, oxepinac, and felbinac; the fenamates, such as mefenamic, meclofenamic, flufenamic, niflumic, and tolfenamic acids; the propionic acid derivatives, such as ibuprofen, naproxen, benoxaprofen, flurbiprofen, ketoprofen, fenoprofen, fenbufen, indoprofen, pirprofen, carprofen, oxaprozin, pranoprofen, miroprofen, tioxaprofen, suprofen, alminoprofen, and tiaprofenic; and the pyrazoles, such as phenybutazone, oxyphenbutazone, feprazone, azapropazone, and trimethazone. Mixtures of these non-steroidal anti-inflammatory agents can also be employed, as well as the pharmaceutically-acceptable salts and esters of these agents.

Analgesics suitable for use with the therapeutic compositions described herein include, but are not limited to, local amine and ester anesthetics. Non-limiting examples of analgesics include lidocaine, mepivacaine, bupivacaine, procaine, chloroprocaine, etidocaine, prilocaine and tetracaine. Ice may also be used. Mixtures of these analgesics can also be employed, as well as the pharmaceutically acceptable salts and esters or these agents. Analgesics may be injected or topically applied (e.g., compounded into an ointment or cream).

Pharmacologically acceptable aqueous vehicles for the compositions of the present disclosure can include, for example, any liquid solution that is capable of dissolving a bile acid or bile salt and is not toxic to the particular individual receiving the formulation. Examples of pharmaceutically acceptable aqueous vehicles include, without limitation, saline, water, and acetic acid. Pharmaceutically acceptable aqueous vehicles are preferably sterile.

The therapeutic compositions described herein can include one or more pharmaceutically-acceptable excipients. Non-limiting examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, phosphatidylcholine, cellulose, sterile water, syrup, and methyl cellulose. Additional excipients suitable for formulation with the therapeutic compositions described herein include penetration enhancers and dispersion agents. Non-limiting examples of dispersion agents that facilitate the dispersion of the pharmacologically active component(s) of the therapeutic compositions in tissue include hyaluronidase and collagenase. Hyaluronidase functions to augment tissue permeability and dispersion of other drugs. Collagenase has been used to isolate adipocytes from subcutaneous fat and does not have lytic effects on adipocytes themselves. Additionally hyaluronidase and collagenase can facilitate healing by accelerating removal of damaged or necrotic tissue (if any) after treatment with any of the therapeutic compositions described herein.

The therapeutic compositions described herein can additionally include lubricating agents such as talc, magnesium stearate, and mineral oil; wetting agents or emulsifying and suspending agents and preserving agents such as methyl- and propylhydroxy-benzoates and benzyl alcohol. The therapeutic compositions described herein can be formulated so as to provide quick, sustained or delayed release of the active ingredient after administration to the patient by employing procedures known in the art.

Methods of Treating Residual Lesions of Vascular Anomalies

The present disclosure relates to therapeutic compositions that comprise at least one pharmacologically-active bile acid or its salt, optionally at least one pharmaceutically-acceptable excipient, and optionally one or more additional active ingredients, analgesics or dispersion agents and their use in treating residual lesions of vascular anomalies. Contemplated vascular anomalies include involuting infantile hemangiomas, involuted infantile hemangiomas, congenital hemangiomas, kaposiform hemangiomendotheliomas (KHE), tufted angiomas, lymphatic malformations, and other vascular anomalies that comprise a residual lesion, i.e., a lesion that is not tumorous and that has some partial fibrous or fibrofatty characteristics.

DCA is a pharmacologically-active bile acid that was approved in 2015 to treat submental fat reduction in adults and is marketed under the trade name KYBELLA®. However, neither DCA nor any other bile acid has been approved to treat any vascular anomaly, and it was quite surprising to the present inventors that DCA and other bile acids could work to treat these maladies. DCA works by disrupting adipocyte cell membranes leading to cell lysis and inflammation. In contrast, vascular anomalies are produced by some localized defect in one or more elements of the vasculature (i.e., arteries, veins, capillaries and lymphatics) and lack the predominantly adipose character for which DCA is indicated and approved. Even when fat cells comprise a part of the residual lesion of a particular vascular anomaly (e.g., FFR), fat cells appear different from localized adipose tissue in that it is fibrofatty, i.e., a mix of fibrous and fat cells. Unsurprisingly, to the best of the inventors' knowledge, there has been no report thus far concerning the administration or effectiveness of a therapeutic composition comprising a bile acid or its salt to treat a a residual lesion of a vascular anomaly.

In particular embodiments, the methods comprise contacting the residual lesion of the vascular anomaly with an effective amount of a composition comprising a bile acid or its salt. As used herein, the terms "treat" and "treatment" refer to the alleviation or amelioration of one or more symptoms or effects associated with the vascular anomaly, prevention, inhibition or delay of the onset of one or more symptoms or effects, lessening of the severity or frequency of one or more symptoms or effects, and/or increasing or trending toward desired outcomes. Desired outcomes of the treatments disclosed herein vary according to the nature of the vascular anomaly and patient profile and are readily determinable to those skilled in the art. Desired outcomes of the disclosed therapies are generally quantifiable measures as compared to a control or baseline measurement (e.g., compared to a healthy area in the same individual) or baseline measurements of, e.g., a lesion prior to treatment with a bile acid or its salt.

By way of example, desired outcomes include measurable indices such as reduction in size or clearance of the lesion, or improvement in the external or cosmetic appearance of the lesion. Quantitative measures of improvement include reduction of the residual lesion in any dimension, reduction in volume of the residual lesion, reduction in number or size of superficial (visible) vessels, reduction of any symptoms, and improvement in quality of life. Qualitative or semi-qualitative measures of improvement include lightening of superficial (visible) vessels, smoothing out of the residual lesion so that more closely resembles surrounding normal tissue/skin, decrease in protuberance, improved skin and soft tissue integrity/feel of residual lesion, and firming/tightening of the lesion. Changes or improvements in response to therapy are generally statistically significant and described by a p-value less than or equal to 0.1, less than 0.05, less than 0.01, less than 0.005, or less than 0.001 may be regarded as significant.

In particular embodiments, the therapeutic composition is administered by injection, for example, by bolus injection. In order to be effective, the composition must contact the vascular anomaly regardless of how the composition is infused. Therapeutic compositions described herein can be injected subcutaneously or infused directly into anomaly. Compositions may be formulated for injection as suspensions, solutions, or emulsions in oily or aqueous vehicles, and can contain formulatory agents such as suspending, stabilizing and/or dispersing agents. Compositions formulated for injection can be packaged in unit dosage form, for example, in ampoules or in multi-dose containers, with an added preservative. In certain embodiments, the the therapeutic composition is administered topically. For example, the therapeutic composition may comprise a cream or ointment comprising an additive such as dimethyl sulfoxide to facilitate passage of the bile acid or salt.

In certain embodiments, compositions formulated for injection can be injected subcutaneously using an area-adjusted dose of about 0.1 mg/cm$^2$, about 0.5 mg/cm$^2$, 1 mg/cm$^2$, 1.5 mg/cm$^2$, or 2 mg/cm$^2$, or 4 mg/cm$^2$, or 8 mg/cm$^2$, or any fraction thereof. Higher area adjusted doses are contemplated as well. As such, the safe and effective use of the therapeutic compositions depend on the use of the correct number and locations for injections, proper needle placement, and administration techniques, which are within the purview of one of ordinary skill in the art.

In certain embodiments, a single treatment can consist of one or more injections, depending upon the total volume or amount of the therapeutic composition, the weight percentage or strength of the bile acid or bile salt, and the area of treatment. For example of 0.2 mL each (of a 1% bile acid/bile salt formulation) up to a total of 10 mL, spaced 1 cm apart in the lesion. Multiple treatments may be administered over the course of hours to years, depending upon the patient's response and tolerance.

In certain embodiments, therapeutic compositions described herein may form part of a packaged article, e.g., an article of manufacture, such as a kit or a system for use in any contemplated method of administration and delivery of the compositions for the treatment of contemplated involuted infantile hemangiomas and other contemplated elastic and vascular tissue disorders. The packaged article can include, optionally, a label(s) and/or instructions for use. Such instructions include directing or promoting, including advertising, use of the article of manufacture. Compositions formulated for injection can be packaged in unit dosage form, for example, in ampoules or in multi-dose containers, optionally with an added preservative.

EXAMPLES

The invention is now described with reference to the following Examples. These Examples are provided for the purpose of illustration only, and the invention is not limited to these Examples, but rather encompasses all variations which are evident as a result of the teachings provided herein.

Example 1

A 12-year-old girl was referred for treatment of an involuted IH. She was concerned about the visual appearance and the feeling of fullness caused by the significant convexity of the tumor. Examination of the right flank revealed a skin-colored oval sagging soft tumor with overlying pinpoint vessels and branching telangiectasia (FIG. 1A-1B). Initial measurement was 0.8 cm high and 7.5 cm wide. Management options including surgical excision and laser treatments were discussed. The patient's mother was apprehensive regarding surgery due to the inherent risks of scarring, nerve damage, infection, bleeding, and tissue necrosis.

As an alternative to these options, the present inventors considered administering DCA to the patient to reduce the protuberance of the mass. The associated risks of DCA administration, as well as off-label use, and lack of pediatric approval were discussed with the patient. Two series of injections were planned.

The site was anesthetized with a topical 40% lidocaine ointment. Following prepping with alcohol, an injection grid modified to overlay the affected tissue was applied. Subsequently, 0.2 mL of DCA concentrated to 2 mg/cm$^2$ was injected at 1 cm intervals using a total of 4.4 mL, followed by the application of ice packs. The patient tolerated the procedure well, and experienced moderate post-injection pain, erythema, bruising, and swelling lasting 24-48 hours.

The first treatment achieved marginal improvement. As planned, injections were repeated 3 months later, using an additional 4.2 mL. The patient returned for evaluation two months after her second injection, and reported significant improvement in visual appearance and degree of protrusion. The FFR measured 0.2 cm high and 6.4 cm wide (FIG. 2A-2B). Some of the visible superficial vessels and telangiectasias in the FFR of IH decreased in size, caliber, and/or lightened in color. Some of the superifical vessels appeared to resolve completely (clinically go away/not visible after treatment) post treatment.

The most common side effects of DCA are injection-site reactions such as pain, swelling, bruising, numbness, erythema, and induration. As was observed in the instant patient, these reactions often improve with subsequent injection series. Nothwithstanding the mechanism of fat destruction and concerns that treatment would increase skin laxity, the present inventors observed that skin tension was either maintained or enhanced in the treated patient.

The disclosure of every patent, patent application, and publication cited herein is hereby incorporated herein by reference in its entirety. While this invention has been disclosed with reference to specific embodiments, other embodiments and variations of this invention can be devised by others skilled in the art without departing from the true spirit and scope of the invention. The appended claims include all such embodiments and equivalent variations.

What is claimed is:

1. A method for the treatment of a residual lesion of a vascular anomaly in a patient in need thereof, the method comprising contacting the residual lesion with a composition comprising a pharmaceutically-acceptable formulation consisting essentially of deoxycholic acid or its salt, wherein the vascular anomaly is selected from the group consisting of involuting infantile hemangioma, involuted infantile hemangioma, congenital hemangioma, kaposiform hemangiomendothelioma, tufted angioma, and lymphatic malformation.

2. The method of claim 1, wherein the vascular anomaly is an involuted infantile hemangioma, which optionally comprises one or more sequelae selected from the group consisting of telangiectasia, fibrofatty residue, and anetoderma.

3. The method of claim 1, wherein the bile acid deoxycholic acid is conjugated to taurine or glycine.

4. The method of claim 1, wherein the composition is administered as an aqueous solution.

5. The method of claim 4, wherein the solution comprises deoxycholic acid at a concentration of about 1% w/v to about 5% w/v.

6. The method of claim 5, wherein the solution comprises deoxycholic acid at a concentration of 1% w/v.

7. The method of claim 1, wherein the solution comprises sodium deoxycholate.

8. The method of claim 1, wherein the composition is administered to the patient more than once.

9. The method of claim 1, wherein the composition is administered intralesionally.

10. The method of claim 1, wherein duration of treatment is at least 2 months.

11. The method of claim 10, wherein the duration of treatment at least 6 months.

12. The method of claim 10, wherein the duration of treatment is at least 1 year.

13. The method of claim 1, wherein the duration of treatment is effective to achieve at least a 5% reduction in the size of the lesion.

14. The method of claim 1, wherein the duration of treatment is effective to achieve at least a 25% reduction in the size of the lesion.

15. The method of claim 1, wherein the duration of treatment is effective to achieve at least a 50% reduction in the size of the lesion.

16. The method of claim 1, wherein the duration of treatment is effective to achieve an improvement in at least one symptom of the lesion.

* * * * *

UNITED STATES PATENT AND TRADEMARK OFFICE
CERTIFICATE OF CORRECTION

PATENT NO. : 11,554,126 B2
APPLICATION NO. : 16/772630
DATED : January 17, 2023
INVENTOR(S) : Cynthia Marie Carver Deklotz et al.

It is certified that error appears in the above-identified patent and that said Letters Patent is hereby corrected as shown below:

In the Claims

Column 10, Line 29, Claim 3, please replace: "The method of claim 1, wherein the bile acid deoxycholic acid is conjugated to taurine or glycine.", with -- The method of claim 1, wherein the deoxycholic acid is conjugated to taurine or glycine. --

Signed and Sealed this
Twenty-first Day of March, 2023

Katherine Kelly Vidal
Director of the United States Patent and Trademark Office